United States Patent [19]

Alexander

[11] Patent Number: 5,095,844
[45] Date of Patent: Mar. 17, 1992

[54] WATER IN OIL DETECTION PLUG

[76] Inventor: Phillip L. Alexander, 1153 SW. 118 Ter., Davie, Fla. 33325

[21] Appl. No.: 655,560

[22] Filed: Feb. 14, 1991

[51] Int. Cl.⁵ .......................... C09K 3/00; G01N 33/18
[52] U.S. Cl. ..................................... 116/206; 422/56; 436/40
[58] Field of Search .................. 116/206; 436/40, 170; 422/56, 60

[56] References Cited

U.S. PATENT DOCUMENTS

| | | | |
|---|---|---|---|
| 2,506,806 | 5/1950 | Metzger | 422/60 X |
| 2,951,461 | 9/1960 | Lockwood | 116/206 |
| 3,000,345 | 9/1961 | Gray, Jr. et al. | 116/206 |
| 3,217,689 | 11/1965 | Knight et al. | 116/206 |
| 3,976,572 | 8/1976 | Reick | 436/40 X |
| 4,063,452 | 12/1977 | Bradshaw | 116/206 X |
| 4,717,671 | 1/1988 | Melpolder | 436/40 X |
| 4,757,710 | 7/1988 | Haynes | |
| 4,789,363 | 12/1988 | Wicklein | |
| 4,803,876 | 2/1989 | Haynes | |

*Primary Examiner*—Daniel M. Yasich
*Attorney, Agent, or Firm*—Shefte, Pinckney & Sawyer

[57] ABSTRACT

A water detection plug for use in a marine engine or the like having lubricants such as oil contained therein including an arrangement for indicating the presence of water in the lubricant when the water is in contact with the plug such that the indicator arrangement presents a first distinct visual appearance when not in contact with water and a second distinct visual appearance different from the first visual appearance when the plug is in contact with water, thereby generating a visual signal which is visible to an observer located outside the device when the lubricant in contact with the plug becomes mixed with water.

15 Claims, 2 Drawing Sheets

WATER IN OIL DETECTION PLUG

BACKGROUND OF THE INVENTION

This invention relates generally to engines which are exposed to or partially submerged in water, and particularly to such an engine that includes a lubrication filler or drain plug which detects the presence of water in the lubricant within the engine and generates a visual signal in response thereto. While the present invention is particularly useful in marine engines which are partially submerged in water, it may also be used in other applications where the detection of water in a lubricant may be desirable.

In outboard or inboard-outboard marine engines, the propeller and its associated drive gears are collectively known as the drive unit and/or lower unit, and it is submerged in water during normal operation. Even though the units are equipped with seals and gaskets to keep out the surrounding water, the seals may become damaged or otherwise fail due to normal wear. This failure can allow water to enter the drive unit and become mixed with the lubricant contained therein. As a result of this contamination of the lubricant by water, the internal components of the drive unit, including its gears, bearings, and propeller shaft, are almost certain to be damaged or destroyed if the condition is allowed to continue. The potential for destruction is hastened in engines used in a saltwater environment. Subsequent repair or replacement of the drive unit can be costly.

Typically, the units include two plugged openings. The first plugged opening is located adjacent the top of the unit and is used as a vent in the adding or draining of lubricant thereto. The other plugged opening is located adjacent the base of the unit and is used to fill the unit and to drain lubricant therefrom. One known method of determining whether water has become mixed with the lubricant in an drive unit is to drain the oil therefrom and examine the oil for presence of water. Water mixed with gear drive lubricant will give the lubricant a milky appearance as opposed to the normal dark appearance of uncontaminated lubricant.

An alternate method of detecting the presence of water in outdrive lubricant is provided by Haynes U.S. Pat. No. 4,757,710 which discloses a sight glass fitted into a hole formed in the side of the drive unit casing. This sight glass allows the visual inspection of the outdrive lubricant without removing the lubricant from the drive unit. The sight glass of Haynes is basically a window. A second Haynes patent, U.S. Pat. No. 4,803,876 discloses the same sight glass as the previous Haynes patent, but the second Haynes sight glass is directed toward manufacturers of drive units in that it requires a hole to be specially formed in the side of the casing of the drive unit during manufacture. Wicklein U.S. Pat. No. 4,789,363, incorporates the sight glass principle of Haynes into a unit more readily adapted to existing marine engines in that the sight glass of Wicklein is configured to replace the aforementioned drain plug on the drive unit.

The sight glass units of the above-mentioned patents allow boating enthusiasts to inspect the condition of the lubricant in the drive unit without draining the lubricant therefrom, making the inspection easier, yet less reliable than draining the lubricant for inspection. The boater still has to make a visual inspection of the lubricant itself and then make a determination, based on the color of the lubricant, whether the lubricant has become fouled by the incursion of water into the drive unit. However, this visual inspection surveys only a very small portion of the outdrive lubricant, namely that which is in contact with the sight glass at the time of inspection. The present state of the art allows at best a rough approximation of the water content, if any, of the gear lubricant in the drive unit of a marine engine.

While these concerns are of particular interest to boating enthusiasts, similar problems may arise in an automotive environment or in other lubricant containing devices which are exposed to water or moisture.

SUMMARY OF THE INVENTION

It is accordingly an object of the present invention to solve the aforementioned problem by providing an easy to use, reliable method of determining whether water has become mixed with lubricant in a marine drive unit or other internally lubricated device. The present invention provides a water detection plug in an outer wall or barrier of a device having a lubricant such as oil contained therein, the plug including a plug body adapted to be mounted in the outer wall or barrier, and an arrangement for indicating the presence of water in the lubricant when the water is in contact with the plug. The indicator arrangement is visible to an observer located outside the device, and is formed of a material having a first condition in which it presents a first distinct visual appearance when not in contact with water and a second condition in which it presents a second distinct visual appearance different from the first visual appearance when the plug is in contact with water, thereby generating a visual signal when the lubricant in contact with the plug becomes mixed with the water. Preferably, the plug body is a T-shaped member having a head portion formed integrally with a shank portion, and the shank portion has threads formed on its exterior surface. The plug body has an axial bore formed therethrough for containing the indicator arrangement.

In the preferred embodiment of the present invention, the material of the indicator arrangement includes an inner contact layer which is a semi-permeable membrane, preferably a cuproammonium cellulose membrane, located at a position within the bore to be in contact with the lubricant. The membrane is permeable to water and impermeable to lubricant. The indicator arrangement also includes an intermediate layer of a material capable of assuming the aforementioned first and second visual appearance conditions. Preferably this material is a paper substrate impregnated with cobalt chloride crystals. The indicator arrangement further includes an outer viewing layer of a material, preferably glass, which permits a visual inspection of the intermediate indication layer from a position outside of the device.

Preferably, the water detection plug of the present invention is configured for use in a marine engine of the type having a submersible drive unit including a propeller and a casing containing drive gears and a lubricant, the casing having at least one threaded hole formed therein for draining the lubricant from the drive unit or for inserting the lubricant into the drive unit, the water detection plug being inserted in the casing in place of the conventional plug used in the casing such that the water detection plug is in contact with the lubricant. The threads on the shank portion of the plug body of the present invention are configured so as to be threaded in correspondence with the threaded hole in the casing to allow the use of the water detection plug as a lubrication drain or filler plug.

As can be seen from the above, the water detection plug of the present invention allows the boating enthusiasts to check for the presence of water in the outdrive lubricant without draining the lubricant from the drive unit. The unreliability problem of the prior art is solved by the ability of the water detection plug of the present invention to actually detect the presence of water in the lubricant and generate a positive visual signal when the lubricant in contact with the plug becomes mixed with water. The presence of water in the lubricant can now be determined without just relying on the judgment of an observer.

DESCRIPTION OF THE PREFERRED EMBODIMENT

Figures 1, 2:
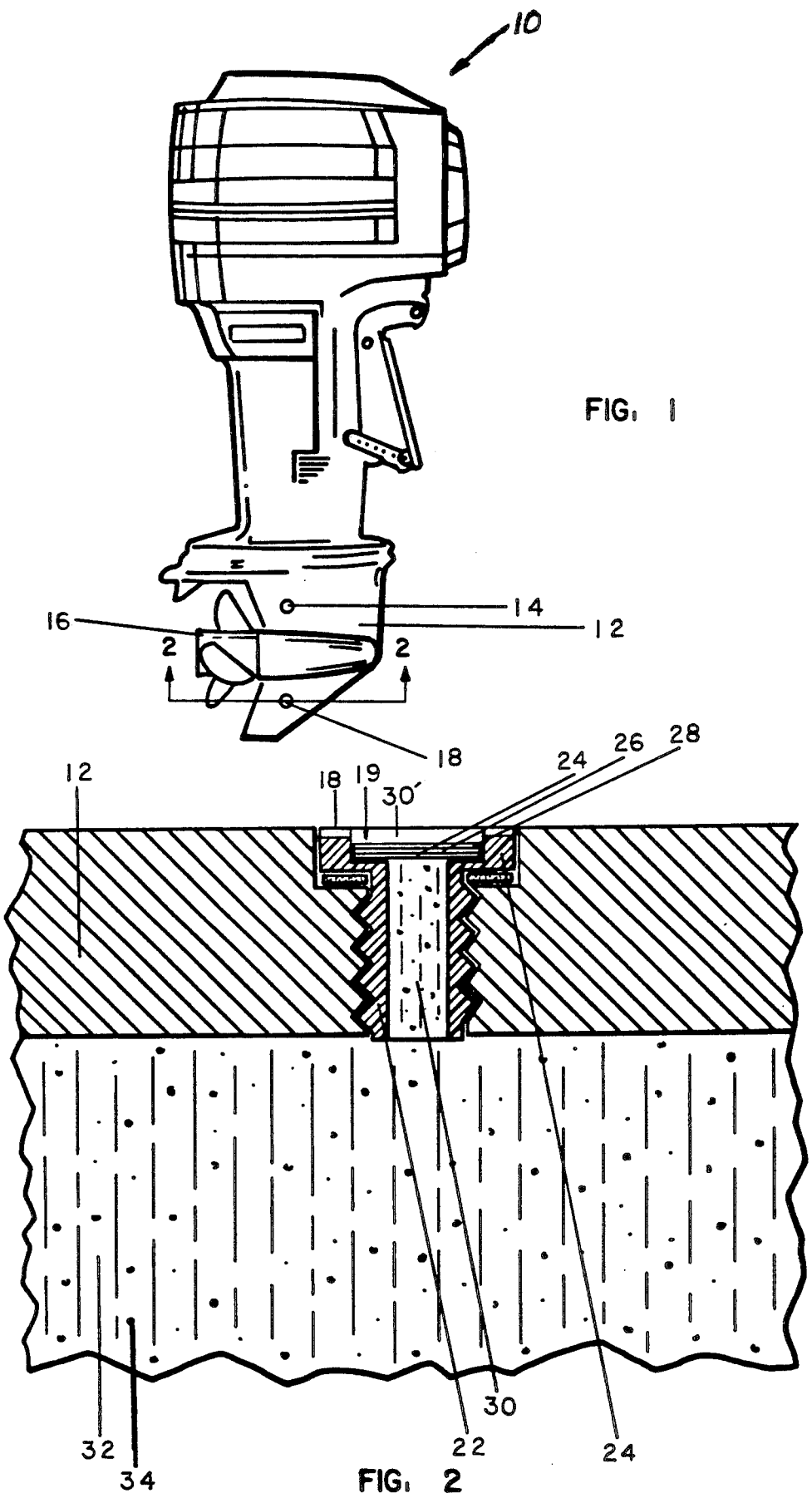
FIG. 1 is an elevational view of an outboard marine engine having a drive unit equipped with the water detection plug according to the preferred embodiment of the present invention.
FIG. 2 is a sectional view of the water detection plug illustrated in FIG. 1 taken through the wall of the drive unit showing the water detection plug installed in a threaded drain or fill opening in the drive unit.

Referring now to the accompanying drawings and particularly FIG. 1, an outboard marine engine is shown generally at 10 and includes an drive unit 12 and a propeller 16. A lubrication filler plug 14 is shown mounted on the drive unit, and a water detection plug 18 of the present invention serves as a lubrication drain plug for the drive unit.

Figure 3:
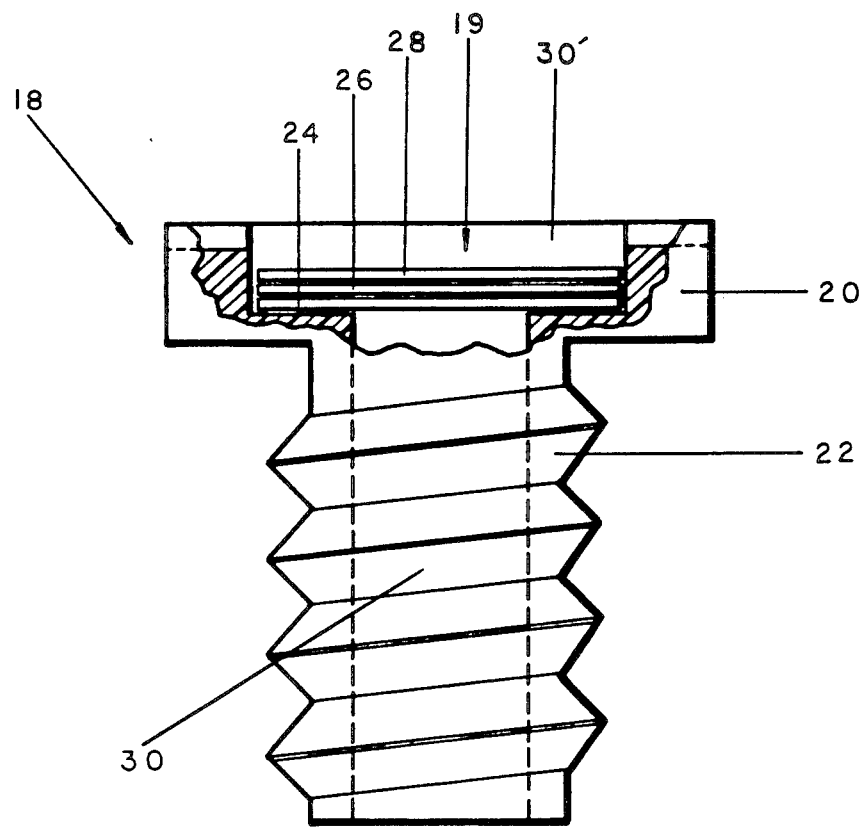
FIG. 3 is an enlarged sectional side view of the water detection plug of the present invention.
Figure 4:
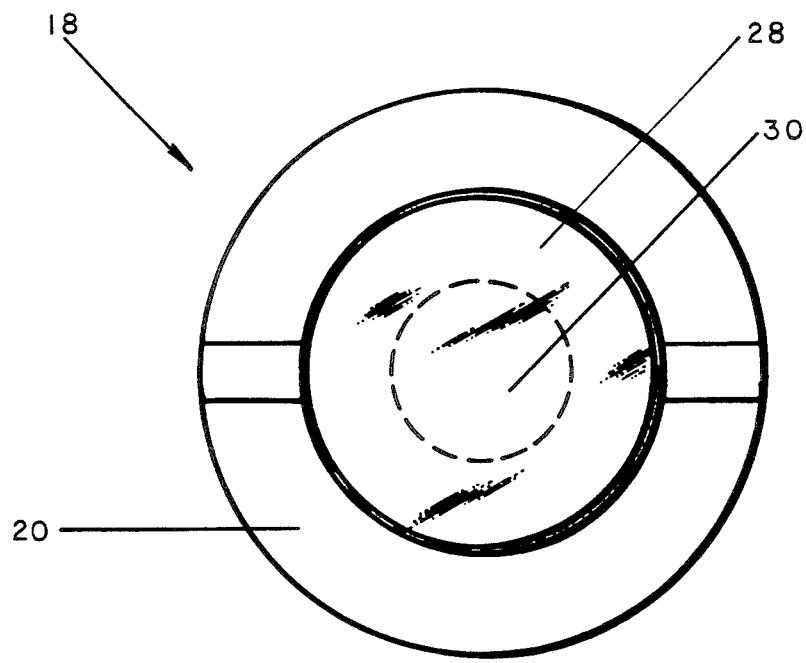
FIG. 4 is a front view of the water detection plug illustrated in FIG. 3.

FIGS. 2-4 best illustrate the preferred embodiment of the water detection plug 18 of the present invention, which is a T-shaped member that includes a head portion 20 containing an indicator arrangement 19 and a shank portion 22 which is preferably threaded. A bore 30 extends through the water detection plug 18 and includes an enlarged recess 30' in the head portion 20 for receiving the indicator arrangement 19 and for providing a passageway for the lubricant 32 to reach the indicator arrangement 19.

The indicator arrangement 19 includes three layers of materials. The first layer is the inner contact layer 24 and includes a semi-permeable membrane which is in contact with the lubricant 32, and which is permeable to water 34 yet impermeable to lubricant 32. In the preferred embodiment of the present invention, the inner contact layer is a cuproammonium cellulose membrane located at a position within the recess 30' to be in contact with the lubricant 32 as best seen in FIG. 2, the detail of such membrane being described in greater detail in U.S. Pat. No. 4,886,603, issued Dec. 12, 1989. The second layer of material is the indicator layer 26 which is formed of a material having a first condition in which it presents a distinct visual appearance when not in contact with water 34 and a second condition in which it presents a second distinct visual appearance different from the first visual appearance when the indicator layer 26 is contacted by water 34. Preferably, the indicator layer 26 is a paper substrate impregnated with cobalt chloride crystals which, when contacted by water 34, change color. The third layer is the viewing layer 28 which is the outermost layer for allowing the indicator layer 26 to be visible to an observer located outside of the drive unit 12. Preferably, the viewing layer 28 is made of glass.

Referring now to FIG. 2, the water detection plug 18 of the present invention is shown mounted in the casing of the drive unit 12. The threaded shank portion 22 is configured so as to mate with the threads of the lubrication drain opening or filler opening formed in the casing of the drive unit 12. When the water detection plug 18 is mounted in the drive unit 12, lubricant 32 travels up the bore 30 where it encounters the inner contact layer 24 of the indicator arrangement 19. Any water 34 present in the lubricant 32 will be passed through the inner contact layer 24 to the indicator layer 26. In the preferred embodiment of the present invention, any water 34 which was passed through the inner contact layer 24 will encounter the paper substrate impregnated with cobalt chloride crystals which undergo reaction and, as a result, undergo a transformation from a first condition in which the indicator layer 26 presents a distinct visual appearance to a second condition in which the indicator layer 26 presents a second distinct visual appearance different from the first visual appearance, namely a distinct color change from an initial blue appearance to a lavender appearance. The viewing layer 28 allows an observer to determine whether the reaction has taken place, thus indicating the presence of water 34 in the lubricant 32.

Thus, once water 34 is detected within the lubricant 32, the lubricant 32 may be drained and replaced with uncontaminated lubricant, and a new water detection plug 18 installed, thereby allowing boating enthusiasts to remain ever vigilant to the presence of water 34 in the lubricant 32 of the drive unit 12 of the marine engine 10 by simply visually checking detection plug 18 at periodic intervals.

It will therefore be readily understood by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

I claim:

1. A water detection plug for use in a marine engine or the like of the type having a casing that is submerged in or exposed to water and that contains a lubricant, said plug comprising a plug body formed with an opening therein that receives said lubricant and adapted to be mounted in the casing and including means for indicating the presence of water in the lubricant when water is in contact with said plug, said indicator means being formed of a material that includes an inner contact layer including a semipermeable membrane located at a position within said opening to be in contact with the lubricant, said membrane being permeable to water and impermeable to lubricant, an intermediate indication layer of material capable of assuming said first and second conditions and an outer viewing layer of a material which permits visual inspection of said indication layer may position outside the casing thereby generating a visual signal when the lubricant in contact with said plug becomes mixed with water.

2. A water detection plug according to claim 1 and characterized further in that said plug body is a T-shaped member having a head portion and a shank portion, said head portion being integral with said shank portion, said shank portion having threads formed on its exterior surface, said plug body opening comprising an axial bore formed to extend axially through said plug body.

3. A water detection plug according to claim 1 and characterized further in that said material of said indicator means includes an inner contact layer including a cuproammonium cellulose membrane located at a position within said bore to be in contact with the lubricant, an intermediate indicator layer of a paper substrate impregnated with cobalt chloride crystals capable of assuming first and second conditions and an outer viewing layer of glass which permits a visual inspection of said indicator layer from a position outside of the casing.

4. A water detection plug according to claim 3 and characterized further in that said threads formed on the exterior surface of said shank portion correspond to threads formed in the wall of the casing so that said plug body may be screwed in and out of mounting relation with the casing to allow said water detection plug to be used as a lubrication plug associated with the engine or other such internally lubricated machine.

5. A water detection plug for use in a marine engine or the like of the type having a submersible drive unit including a propeller and a casing containing drive gears and a lubricant, the casing having at least one threaded hole formed therein for draining the lubricant from the drive unit or for inserting the lubricant into the drive unit, said plug comprising a T-shaped plug body including a head portion, a shank portion integral with said head portion, and means for indicating the presence of water in the lubricant when water is in contact with said plug; said plug body having an axial bore extending therethrough, and containing said indicator means so that the lubricant is exposed to said indicator means through said bore; said indicator means including an inner contact layer of a cuproammonium cellulose membrane located at a position within the bore to be in contact with the lubricant, said membrane being permeable to water and impermeable to lubricant; an intermediate indicator layer of a paper substrate material impregnated with cobalt chloride crystals, said indicator layer having a first condition in which it presents a first distinct visual appearance when not in contact with water and a second condition in which it presents a second distinct visual appearance different from said first visual appearance when said plug is in contact with water; and an outer viewing layer of glass which permits a visual inspection of said indicator layer from a position outside of the casing, said shank portion having threads formed on its exterior surface capable of mating with the threaded hole in the casing to allow use of said water detection plug as a lubricant drain or filler plug.

6. A water detection plug for use in a marine engine or the like of the type having a submersible drive unit including a propeller and a casing containing drive gears and a lubricant, the casing having at least one threaded hole formed therein for draining the lubricant from the drive unit or for inserting the lubricant into the drive unit, said plug comprising a plug body formed with an opening therein that receives the lubricant and adapted to be mounted in the casing and including means for indicating the presence of water in the lubricant when water is in contact with said plug, said indicator means being formed of a material that includes an inner contact layer including a semipermeable membrane located at a position within said opening to be in contact with the lubricant, said membrane being permeable to water and impermeable to lubricant, an intermediate layer of material capable of assuming first and second conditions and an outer viewing layer of a material which permits visual inspection of said indicator layer from a position outside the casing thereby generating a visual signal when the lubricant in contact with said plug becomes mixed with water, said plug body having threads corresponding to the threaded hole formed in the casing to allow use of said water detection plug as a lubrication drain or filler plug.

7. A water detection plug according to claim 6 and characterized further in that said plug body is a T-shaped member having a head portion and a shank portion, said head portion being integral with said shank portion, said shank portion having threads formed on its exterior surface, said plug body opening comprising an axial bore formed to extend axially through said plug body.

8. A water detection plug according to claim 6 and characterized further in that said material of said indicator means includes an inner contact layer including a cuproammonium cellulose membrane located at a position within said bore to be in contact with the lubricant, an intermediate layer of a paper substrate impregnated with cobalt chloride crystals capable of assuming first and second conditions and an outer viewing layer of glass which permits a visual inspection of said indicator layer from a position outside of the device.

9. A water detection plug for use in a lubricant containing vessel of the type having a casing such as the crankcase of an engine, a transmission, or the like, said plug comprising a plug body formed with an opening therein that receives said lubricant and adapted to be mounted in the casing and includes means for indicating the presence of water in the lubricant when water is in contact with said plug, said indicator means being formed of a material that includes an inner contact layer including a semipermeable membrane located at a position within said opening to be in contact with the lubricant, said membrane being permeable to water and impermeable to lubricant, an intermediate indication layer of material capable of assuming first and second conditions and an outer viewing layer of a material which permits visible inspection of said indication layer from a position outside the casing.

10. A water detection plug according to claim 9 and characterized further in that said plug body is a T-shaped member having a head portion and a shank portion, said head portion being integral with said shank portion, said shank portion having threads formed on its exterior surface, said plug body opening comprising an axial bore formed to extend axially through said plug body.

11. A water detection plug according to claim 9 and characterized further in that said material of said indicator means includes an inner contact layer including a cuproammonium cellulose membrane located at a position with said bore to be in contact with the lubricant, an intermediate indicator layer of a paper substrate impregnated with cobalt chloride crystals capable of assuming first and second conditions and an outer viewing layer of glass which permits a visual inspection of said indicator layer from a position outside the casing.

12. A water detection plug according to claim 11 and characterized further in that said threads formed on the exterior surface of said shank portion correspond to threads formed in the wall of the casing so that said plug body may be screwed in and out of mounting relation with the casing to allow said water detection plug to be used as a lubrication plug associated with the engine or other such internally lubricated machine.

13. A water detection plug for use in a lubricant containing vessel of the type having a casing such as the crank case of an engine, a transmission, or the like, the casing having at least one threaded hole formed therein for draining the lubricant from the drive unit or for inserting the lubricant into the drive unit, said plug comprising a plug body formed with an opening therein that receives the lubricant and adapted to be mounted in the casing and including means for indicating the presence of water in the lubricant when the water is in contact with said plug, said indicator means being formed of a material that includes an inner layer within said opening to be in contact with the lubricant, said membrane being permeable to water and impermeable to lubricant, an intermediate layer of material capable of assuming first and second conditions and an outer viewing layer of a material which permits visual inspection of said indicator layer from a position outside the casing thereby generating a visual signal when the lubricant in contact with said plug becomes mixed with water, said plug body having threads corresponding to the threaded hold formed in the casing to allow use of said water detection plug as a lubrication drain or filler plug.

14. A water detection plug according to claim 13 and characterized further in that said plug body is a T-shaped member having a head portion and a shank portion, said head portion being integral with said shank portion, said shank portion having threads formed on its exterior surface, and said plug body having said bore formed to extend axially therethrough.

15. A water detection plug according to claim 13 and characterized further in that said material of said indicator means includes an inner contact layer including a cuproammonium cellulose membrane located at a position within said bore to be in contact with the lubricant, an intermediate layer of a paper substrate impregnated with cobalt chloride crystals capable of assuming first and second conditions and an outer viewing layer of glass which permits a visual inspection of said indicator layer from a position outside of the device.

* * * * *

UNITED STATES PATENT AND TRADEMARK OFFICE
CERTIFICATE OF CORRECTION

PATENT NO. : 5,095,844

DATED : Mar. 17, 1992

INVENTOR(S) : Phillip L. Alexander

It is certified that error appears in the above-identified patent and that said Letters Patent is hereby corrected as shown below:

Column 1, Line 21, after "wear" add -- and tear --.

Column 1, Line 56, after "4,789,363" delete -- , --.

Column 3, Line 34, delete "an" and insert -- a -- therefor.

Column 5, Line 9, delete "may" and insert -- from a -- therefor.

Column 6, Line 61, delete "visible" and insert -- visual -- therefor.

Column 7, Line 7, delete "with" (first occurrence) and insert -- within -- therefor.

Column 8, Line 11, delete "hold" and insert -- hole -- therefor.

Signed and Sealed this

Thirty-first Day of August, 1993

*Attest:*

BRUCE LEHMAN

*Attesting Officer*     *Commissioner of Patents and Trademarks*